(12) United States Patent
Karam et al.

(10) Patent No.: US 10,370,156 B2
(45) Date of Patent: Aug. 6, 2019

(54) ONE-PIECE SAFETY TUBE CLOSURE WITH FILM ELEMENT

(71) Applicant: Becton, Dickinson and Company, Franklin Lakes, NJ (US)

(72) Inventors: Jean-Pierre R. Karam, Wyckoff, NJ (US); Judith A. Reichenbach, Pompton Plains, NJ (US); Craig Owen Russ, Wayne, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 66 days.

(21) Appl. No.: 14/454,232

(22) Filed: Aug. 7, 2014

(65) Prior Publication Data

US 2016/0039578 A1 Feb. 11, 2016

(51) Int. Cl.
| | |
|---|---|
| *A61B 5/15* | (2006.01) |
| *B65D 39/00* | (2006.01) |
| *B29C 65/70* | (2006.01) |
| *B01L 3/00* | (2006.01) |
| *B65D 51/00* | (2006.01) |
| *A61B 5/154* | (2006.01) |

(52) U.S. Cl.
CPC ...... *B65D 39/0052* (2013.01); *A61B 5/15003* (2013.01); *A61B 5/154* (2013.01); *A61B 5/150259* (2013.01); *A61B 5/150351* (2013.01); *B01L 3/50825* (2013.01); *B29C 65/70* (2013.01); *B65D 51/002* (2013.01); *B01L 2200/0689* (2013.01); *B01L 2300/042* (2013.01); *B01L 2300/044* (2013.01); *B01L 2300/049* (2013.01)

(58) Field of Classification Search
CPC .. B65D 41/0414; B65D 51/02; B01L 3/50825
See application file for complete search history.

(56) References Cited

U.S. PATENT DOCUMENTS

| | | | |
|---|---|---|---|
| 3,874,367 A | | 4/1975 | Ayres |
| 4,044,589 A | * | 8/1977 | Waimsley ............... B21D 51/16 29/888.012 |
| 4,254,884 A | * | 3/1981 | Maruyama ........... B65D 51/002 215/232 |
| 4,320,769 A | | 3/1982 | Eichhorn et al. |
| 4,741,446 A | | 5/1988 | Miller |
| 4,991,104 A | | 2/1991 | Miller |

(Continued)

FOREIGN PATENT DOCUMENTS

| | | |
|---|---|---|
| DE | 3940461 A1 | 6/1991 |
| JP | 5759536 A | 4/1981 |

(Continued)

*Primary Examiner* — Jeffrey R Allen
(74) *Attorney, Agent, or Firm* — The Webb Law Firm (57) ABSTRACT

A closure having enhanced oxygen barrier capabilities includes a cap body formed from a first material, the cap body defining a cavity therethrough, a stopper formed from a second material, the second material being different than the first material and disposed within the cavity, and a barrier layer formed from a third material, the third material being different than at least the second material and associated with at least one of the cap body and the stopper. A container assembly including a closure and a method of forming the closure is also provided.

40 Claims, 4 Drawing Sheets

(56) References Cited

U.S. PATENT DOCUMENTS

| | | | |
|---|---|---|---|
| 5,019,243 A | 5/1991 | McEwen et al. | |
| 5,328,473 A | 7/1994 | Fayngold et al. | |
| 5,494,170 A | 2/1996 | Burns | |
| 5,632,396 A | 5/1997 | Burns | |
| 5,860,937 A | 1/1999 | Cohen | |
| 5,957,822 A * | 9/1999 | Bienhaus | B01L 3/5082 29/453 |
| 6,382,441 B1 * | 5/2002 | Carano | B01L 3/50825 215/232 |
| 6,716,396 B1 * | 4/2004 | Anderson | B01L 3/0275 215/232 |
| 6,893,612 B2 * | 5/2005 | Kacian | B01L 3/50825 215/247 |
| 2002/0079284 A1 | 6/2002 | Carano | |
| 2007/0034592 A1 | 2/2007 | Pavlovic et al. | |
| 2009/0308184 A1 * | 12/2009 | Blekher | A61B 5/1411 73/864.63 |
| 2010/0113976 A1 * | 5/2010 | Wahl | B01L 3/50825 600/573 |

FOREIGN PATENT DOCUMENTS

| | | |
|---|---|---|
| JP | 61146251 U | 9/1986 |
| JP | H10147357 A | 6/1998 |
| JP | 5559640 H | 7/2014 |
| WO | 2009035685 A1 | 3/2009 |
| WO | 2010121772 A1 | 10/2010 |

* cited by examiner

ONE-PIECE SAFETY TUBE CLOSURE WITH FILM ELEMENT

BACKGROUND OF THE INVENTION

Field of the Invention

The present invention is directed to a closure designed to hold a vacuum in an evacuated container and more particularly, to a one-piece closure containing multiple components formed in a single molding process. The invention is also directed to a closure including a foil or film that enhances the oxygen barrier properties of the evacuated container.

Description of Related Art

A commonly used method for collecting biological specimens, such as blood, is the employment of a needle assembly in conjunction with an evacuated container. The evacuated container provides the pressure differential necessary to facilitate flow and collection of the specimen through the needle assembly into the container. An example of an evacuated container used for specimen collection is the VACUTAINER® brand tube commercially available from Becton, Dickinson and Company. The evacuated tubes may be supplied with various additives to prepare the specimen for a particular test. The tubes may also be evacuated to a selected pressure that is less than atmospheric pressure to provide a preselected volume of drawn specimen. The evacuated tube is typically sealed with a pierceable closure which is capable of resealing after puncture and receipt of the specimen.

One type of needle assembly that can be used with an evacuated container can include a tubular body that holds a standard double-ended hollow needle at its distal end with one end, or a non-patient end, of the needle extending into the tube and the other end, or the patient end, of the needle extending out of the tube. The patient end of the needle is configured for connection to a specimen source, such as a patient's vein. The tubular body is configured to receive the evacuated container such that the pierceable closure is pierced by the non-patient end of the needle and the biological sample is drawn from the patient into the container by means of the vacuum within the container.

One type of pierceable closure can comprise multiple parts that are formed in separate molding steps and then assembled together. The multiple parts can include an outer cap body portion and an inner elastomeric pierceable portion that is designed to seal the interior portion of the container. The elastomeric material is of a type that can reseal after piercing and removal of the needle upon completion of specimen collection. Evacuated containers often have a limited shelf life because over time, oxygen can leak through the closure, reducing the effectiveness of the vacuum held within the container.

Expiration dates are determined through shelf-life testing performed under known environmental conditions. Shelf life of an evacuated tube is defined by the stability of the additive, as well as vacuum retention. If the environmental conditions under which evacuated tubes are stored are not consistent with those recommended by the manufacturer, it is possible that the draw volume of the tubes may be affected.

There is a need in the art for a multiple component one-piece closure that can be formed in a single molding process, thus reducing production costs, and which uses less molding materials, thus reducing raw material costs. There is also a need in the art for a closure having enhanced oxygen barrier properties increasing the shelf life of the evacuated container.

SUMMARY OF THE INVENTION

In accordance with an embodiment of the present invention, a closure for use with a specimen collection container includes a cap body formed from a first material, the cap body defining a cavity therethrough. The closure further includes a stopper formed from a second material which is different from the first material, the stopper being disposed within the cavity. The closure assembly also includes a barrier layer formed from a third material, which is different from at least the first material, and which is associated with at least one of the cap body and/or the stopper. The barrier layer can be disposed across at least a portion of the cavity. According to one embodiment, the bather layer can isolate a portion of the cap body from a portion of the stopper. According to another embodiment, the bather layer can isolate a first portion of the stopper from a second portion of the stopper.

According to one design, the cap body, the stopper, and the barrier layer can be formed in a multi-shot molding process. This multi-shot molding process can be interrupted to apply the barrier layer within a portion of the stopper to isolate the first portion of the stopper from the second portion of the stopper.

According to another design, the cap body and the stopper can be formed in a two-shot molding process and the barrier layer can be applied in a post-molding process. The barrier layer is applied to cover at least a portion of the opening defined by the top portion of the cap and/or a top portion of the stopper.

The cap body can include an inward rim extending into the cavity and the barrier layer can be in contact with a portion of the inward rim and a portion of the stopper. According to one embodiment, the barrier layer can be heat sealed to the inward rim, the stopper, or both. It can be appreciated that the barrier layer can be secured to the inward rim and/or stopper by other well-known techniques.

According to yet another embodiment, a seal ring can be positioned within the opening defined by the top portion of the cap and adjacent the bather layer. In this embodiment, the inward rim can be a stepped member having a first portion for receiving a portion of the stopper and a second portion for contacting the bather layer such that the barrier layer is sandwiched between the seal ring and the second portion.

According to still another embodiment, the barrier layer can include a bottom surface positioned adjacent a top portion of the inward rim and a portion of the stopper material is positioned adjacent a top surface of the barrier layer to mechanically lock the barrier layer within a portion of the closure. According to another embodiment, the inward rim portion can include apertures extending therethrough and a top surface of the barrier layer can be coined to a bottom surface of the inward rim. The barrier layer used in the coining process can be applied along with a first shot of the stopper material, overmolded onto a portion of the stopper material, applied with the second shot of the stopper material, or the individual components of the stopper and the barrier layer can be separately assembled and the bather layer can be coined to one or both of the stopper components. According to still another embodiment, the bather layer can be provided on a bottom surface of the stopper.

According to one embodiment, the first material can be high density polyethylene (HDPE) or low density polyethylene (LDPE), the second material can be a thermoplastic elastomer, such as a thermoplastic elastomer capable of resealing after piercing by a needle cannula, and the third material can be at least one of a polymeric and metal based film or a foil structure. The third material can have a thickness of approximately 0.005 mm and can be formed from a material that is substantially oxygen impermeable. According to one embodiment, the third material can be polyethylene terephthalate (PET) or ethylene vinyl alcohol (EVOH). According to another embodiment, the third material can comprise a multi-layer laminate having a central layer formed from polyethylene terephthalate (PET) or ethylene vinyl alcohol (EVOH) sandwiched between at least two polyethylene layers. It can be appreciated that the first, second, and third materials can be formed from other well-known materials having the appropriate physical characteristics to perform their intended function.

The barrier layer can include one or more of a weak spot, a cross-cut, and a slit to facilitate entrance of a needle cannula therethrough during collection of a specimen sample.

In accordance with another embodiment of the present invention, a container assembly comprises a collection container having a closed bottom, an open top portion, and a sidewall extending therebetween, the collection container defining an interior adapted to receive a specimen sample therein. The container assembly further includes a closure for closing the open top portion of the collection container. The closure comprises a cap body formed from a first material, the cap body defining a cavity therethrough, a stopper formed from a second material, the second material being different from the first material, and disposed within the cavity, and a barrier layer formed from a third material, the third material being different from at least the first material, and associated with at least one of the cap body and the stopper.

According to one design, the barrier layer can be disposed across at least a portion of the cavity. According to another design, the barrier layer can isolate a portion of the cap body from a portion of the stopper. According to yet another design, the barrier layer can isolate a first portion of the stopper from a second portion of the stopper. According to still another design, the barrier layer can be provided on a bottom surface of the stopper. The barrier layer can be substantially oxygen impermeable.

In accordance with another embodiment of the invention, a method of forming a closure for closing and sealing a container comprises providing a cap body formed from a first material, the cap body defining a cavity therethrough, providing a stopper formed from a second material, the second material being different than the first material, and disposed within the cavity, providing a barrier layer formed from a third material, the third material being different from at least the first material, and associated with at least one of the cap body and the stopper; and assembling the cap body, the stopper, and the barrier layer together to form a closure.

According to one embodiment, the cap body, the stopper, and the barrier layer can be formed in a multi-shot molding process. According to another embodiment, the cap body and the stopper can be formed in a two-shot molding process and the barrier layer can be applied in a post-molding process.

According to one design, the barrier layer can be applied to cover at least a portion of an opening defined by a top portion of the cap and/or a top portion of the stopper. The cap body can include an inward rim extending into the cavity and the barrier layer can be in contact with a portion of the inward rim and a portion of the stopper. According to another design, the barrier layer can be provided on a bottom surface of the stopper.

The barrier layer can be at least one of heat sealed, secured with a seal ring, mechanically sealed and/or coined to at least one of the cap body and stopper. The barrier layer can be formed from a material that is substantially oxygen impermeable.

DESCRIPTION OF THE PREFERRED EMBODIMENTS

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 1:
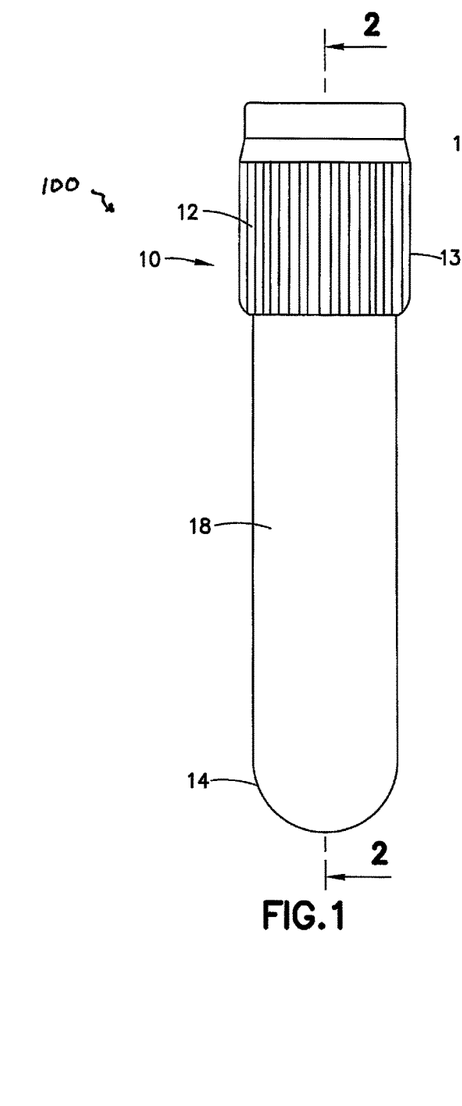
FIG. 1 is a front elevation view of a specimen collection container including a one-piece tube closure in accordance with an embodiment of the present invention.
Figure 2:
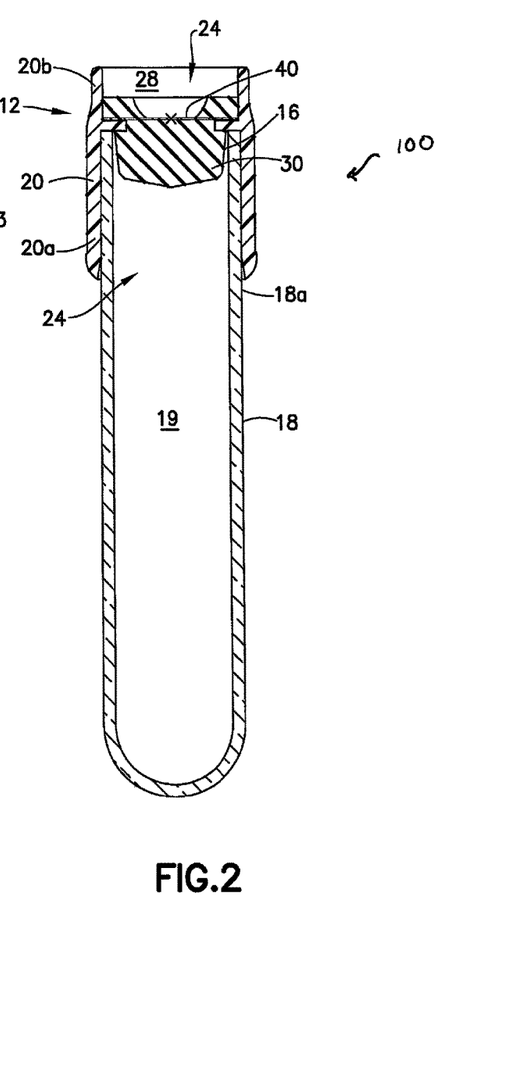
FIG. 2 is a cross-sectional view of the specimen collection container and closure taken along line 2-2 of FIG. 1 in accordance with an embodiment of the present invention.

Reference is now made to FIGS. 1-2 which show a specimen collection container, generally indicated as 10, including a closure assembly 12 for closing and sealing the container 10. The container 10 can be an evacuated container configured for use with a needle assembly for obtaining a biological specimen, such as blood, from a patient. The container can have a closed bottom 14, an open top portion 16, and a sidewall 18 extending therebetween and defining a chamber 19 for receiving the biological specimen therein. The closure assembly 12 cooperates with the open top portion 16 to seal a vacuum within the container 10 at a level to provide a preselected volume of blood drawn.

Figure 3:
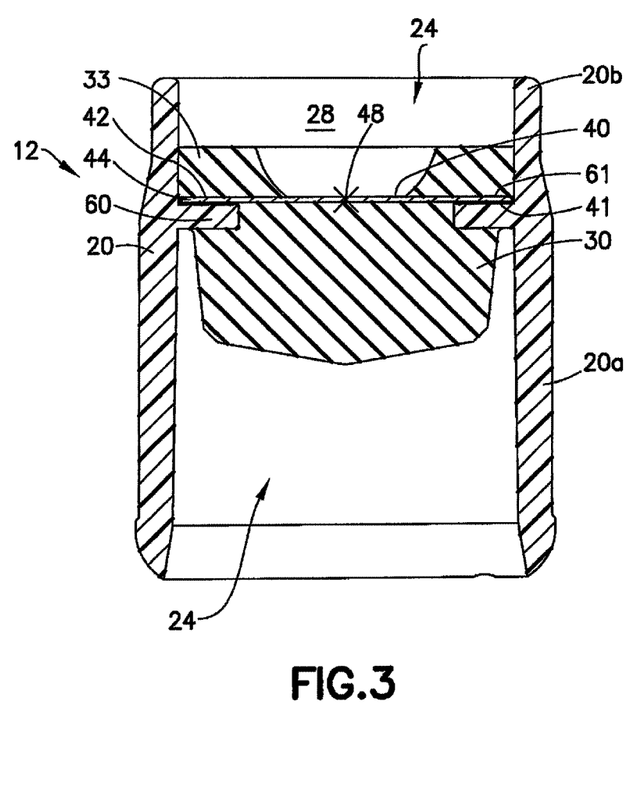
FIG. 3 is an exploded cross-sectional side view of the tube closure of FIG. 2 in accordance with an embodiment of the present invention.

Referring now to FIGS. 2-3, the closure assembly 12 includes a cap body 20 formed from a first material, a stopper 30 formed from a second material that is different than the first material, and a barrier layer 40 formed from a third material that is different from the first material and the second material.

With continuing reference to FIGS. 2-3, the cap body includes first leg portions 20a which are configured to cooperate with an outer surface 18a of the sidewall 18 of the container 10, and second leg portions 20b which extend above the open top portion 16 of the container 10 when the closure assembly 12 is positioned on the container 10. The first leg portions 20a and second leg portions 20b of the cap body 20 define a cavity, generally indicated as 24, extending therethrough. The second leg portions 20b of the cap body 20 define an opening 28. The cavity 24 is in communication with the opening 28. The closure assembly 12 further includes the stopper 30 formed from a second material and disposed within the cavity 24. The stopper 30 is configured for sealing the container 10 and for resealing after puncturing by a needle (not shown) during collection of a specimen. The closure assembly 12 also includes a barrier layer 40 formed from a third material which is associated with at least one of the cap body 20 and/or the stopper 30. The barrier layer 40 is configured for cooperating with the stopper 30 to seal the container 10. The cap body 20, the stopper 30, and the barrier layer 40 can be assembled together to form a one-piece closure assembly 12.

The barrier layer 40 can be disposed across at least a portion of the cavity 24, can isolate a portion of the cap body 20 from a portion of the stopper 30, or can isolate a first portion or top portion 32 of the stopper 30 from a second portion or body 35 of the stopper 30.

According to one design, the cap body 20, the stopper 30, and the barrier layer 40 can be formed in a multi-shot molding process. This multi-shot molding process can be interrupted to apply the barrier layer within a portion of the stopper 30. According to another design, the cap body 20 and the stopper 30 can be formed in a two-shot molding process and the barrier layer 40 can be applied in a post-molding process. It can be appreciated that the cap body 20, the stopper 30, and the barrier layer 40 can be molded and/or assembled according to any well know process to form the one-piece closure assembly 12.

The collection container 10 can be formed from a single layer or multiple layers of different materials as known in the art to optimize the water and vapor barrier properties of the container. Glass containers provide the longest shelf life as they maintain the vacuum draw of the container but are seldom used due to economic and safety issues. Examples of plastic materials that can be used to form the container include, but are not limited to, substantially transparent thermoplastic materials such as polycarbonate, polypropylene, polyehtyleneterephalate (PET), and the like.

Suitable materials for the cap body 20 include, but are not limited to, polypropylene, polyvinylchloride, polyethylene, and the like. According to one embodiment, the cap body 20 can be formed from high density polyethylene (HDPE) or low density polyethylene (LDPE).

The stopper 30 can be formed from any known thermoplastic elastomer. Examples of thermoplastic elastomers that can be used for the stopper 30 include, but are not limited to, silicone rubber, natural rubber, styrene butadiene rubber (SBR), ethylene-propylene dimmer monomer (EPDM), polychloroprene, and the like. According to one embodiment, the second material of the stopper can be formed from a thermoplastic elastomeric material that is free from di(2-ethylhexyl)phthalate (DEHP).

According to the design shown in FIGS. 3, 5, 6, and 7, the barrier layer 40 can be applied to cover at least a portion of the opening 28 defined by the top portion or second legs 20b of the cap body 20 and/or a top portion 32 of the stopper 30.

Figure 6:
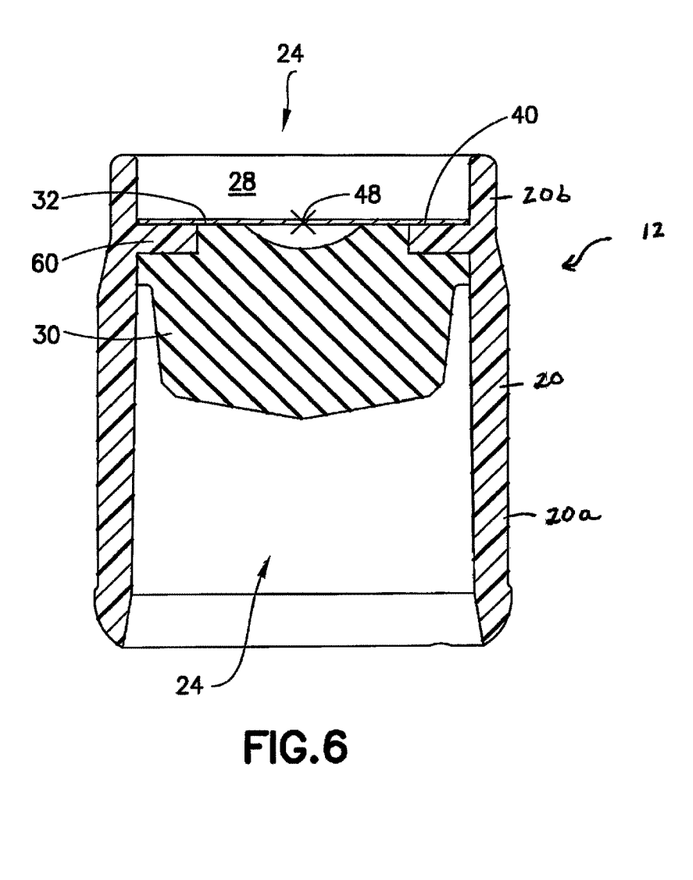
FIG. 6 is a cross-sectional side view of a tube closure for use with the specimen collection container of FIG. 1 in accordance with an embodiment of the present invention.
Figure 7:
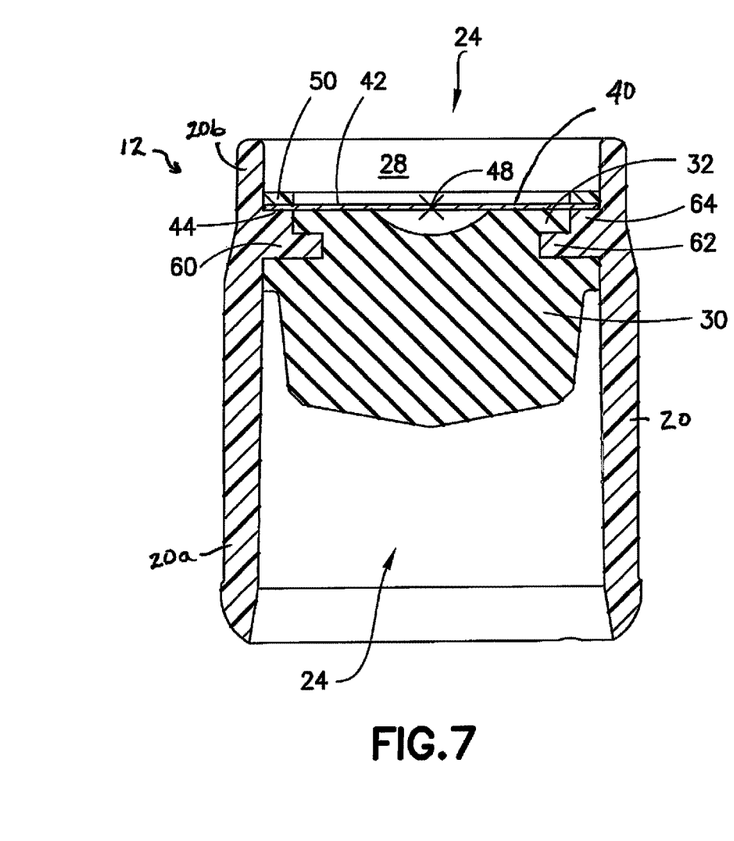
FIG. 7 is a cross-sectional side view of a tube closure for use with the specimen collection container of FIG. 1 in accordance with an embodiment of the present invention.

With continuing reference to FIGS. 3-4 and 6-8, the cap body 20 can include an inward rim 60 extending into the cavity 24. As shown in FIGS. 3, 6, and 7, the barrier layer 40 can be placed in contact with a portion of the inward rim 60 and a portion of the stopper 30. According to one embodiment, the barrier layer 40 can be heat sealed, welded, or adhesively secured to the inward rim 60, the stopper 30, or both. It can be appreciated that the barrier layer 40 can be secured to the inward rim 60 and/or stopper by other well-known techniques.

In addition to the heat seal and/or in an alternative design, as shown in FIG. 3, the barrier layer 40 can include a bottom surface 41 positioned adjacent a top portion 61 of the inward rim 60 and additional stopper material or a first portion 33 of stopper material may be provided adjacent a top surface 42 of the barrier layer 40 to sandwich a portion 44 of the barrier layer 40 between this additional stopper material 33 and the inward rim 60 to mechanically lock the barrier layer 40 therebetween within the closure 12.

Figure 4:
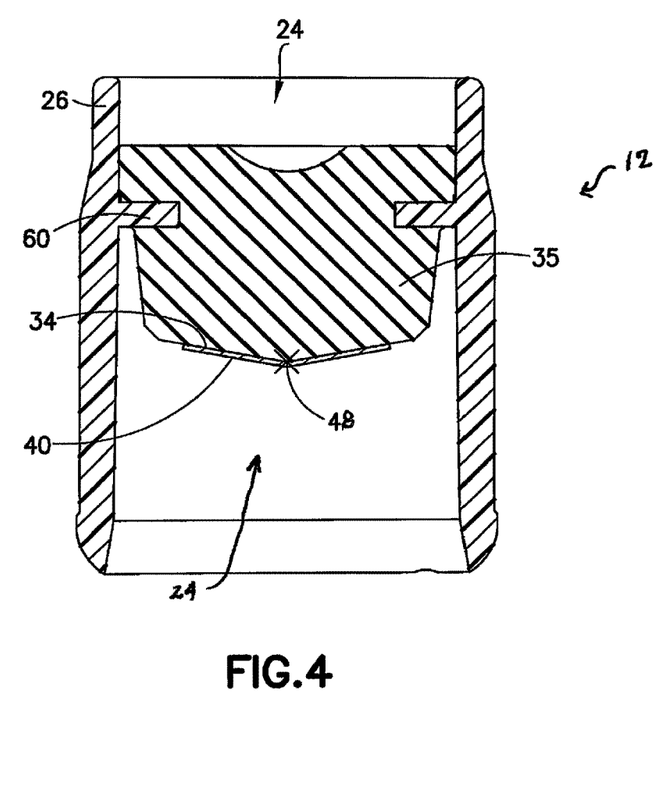
FIG. 4 is a cross-sectional side view of a tube closure for use with the specimen collection container of FIG. 1 in accordance with an embodiment of the present invention.

According to another design, as shown in FIG. 4, the barrier layer 40 can be applied to a portion of the stopper 30 adjacent an open top portion 16 of the container 10. The barrier layer 40 can be applied by any well-known technique as discussed above.

With continuing reference to FIG. 7, a seal ring 50 can be positioned within the opening defined by the top portion or second legs 20b of the cap body 20 and adjacent to the top surface of the barrier layer 40 to secure the barrier layer 40 to the inward rim 60 and/or top portion 32 of the stopper 30. In this embodiment, the inward rim 60 can be a stepped member having a first portion 62 for receiving a portion of the stopper 30 and a second portion 64 for contacting the barrier layer 40 such that the barrier layer 40 is sandwiched between the seal ring 50 and the second portion 64.

Figure 5:
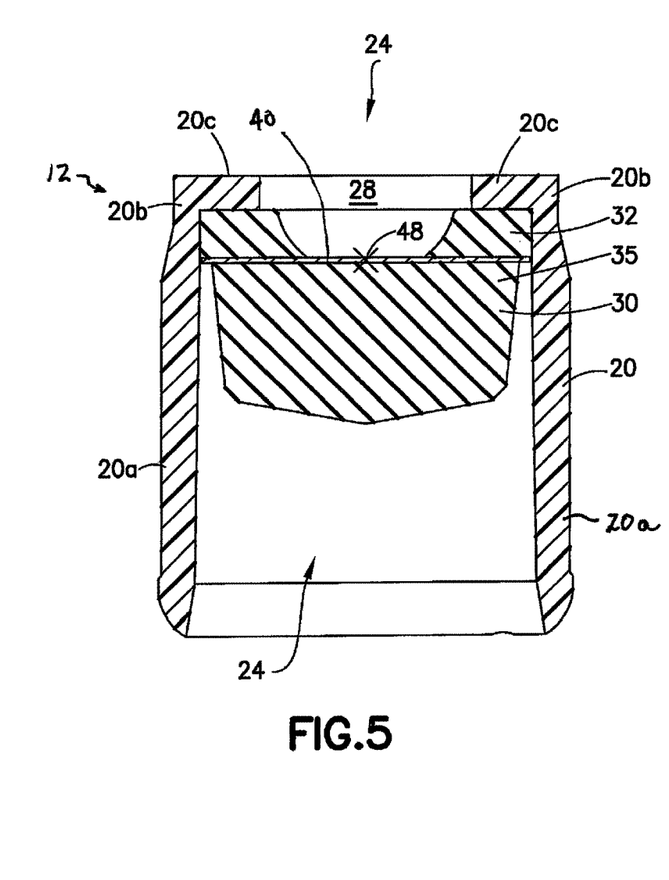
FIG. 5 is a cross-sectional side view of a tube closure for use with the specimen collection container of FIG. 1 in accordance with an embodiment of the present invention.
Figure 8:
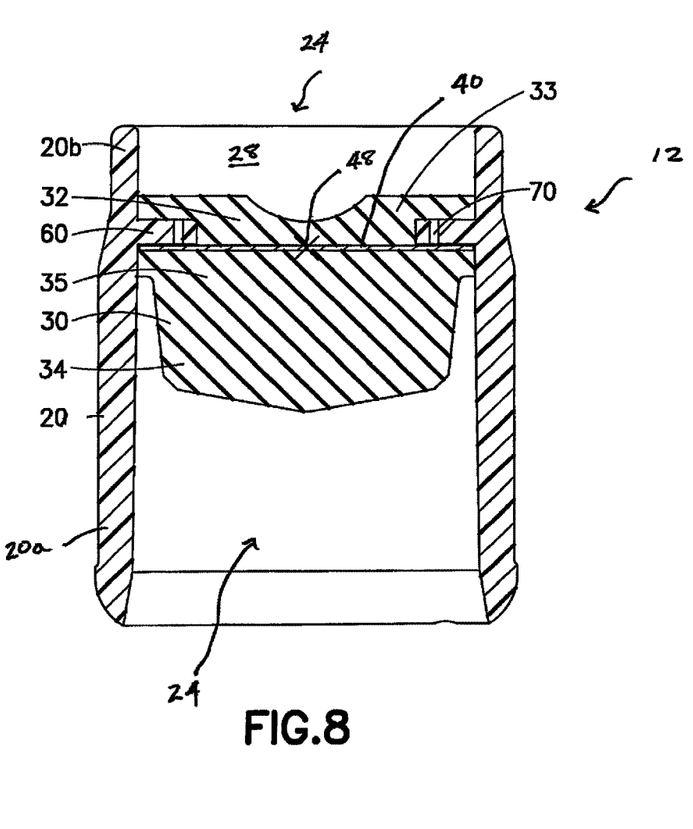
FIG. 8 is a cross-sectional side view of the tube closure for use with the specimen collection container of FIG. 1 in accordance with an embodiment of the present invention.

According to yet another design as shown in FIGS. 5 and 8, the barrier layer 40 can be positioned within a body 35 of the stopper 30. In the design shown in FIG. 5, the multi-shot molding process forming the stopper 30 can be interrupted such as via an in-mold transfer step or a coining process to apply the barrier layer 40 within a portion or within the body 35 of the stopper 30. The barrier layer 40 then becomes an integral component of the stopper 30.

In the design shown in FIG. 5, the second leg 20b can include a third leg 20c which extends into and/or toward the cavity 24 and opening 28 created by the cap body 20. This third leg 20c can cooperate with the top 32 of the stopper 30 to secure the stopper 30 within the cap body 20. It can be appreciated that the stopper 30 can be secured to third leg 20c by any well-known technique including welding, molding, fusing, adhesive application, and the like.

In the design shown in FIG. 8, the stopper 30 can be formed from a first portion or top portion 33 and a second portion or bottom portion 34. According to one embodiment, the second portion 34 of the stopper 30, and the barrier layer 40 are positioned such that the top surface 42 of the barrier layer is located adjacent a bottom surface of the inward rim 60 of the cap body 20. The first portion 33 of the stopper 30 can be applied as additional stopper material 33 adjacent to the inward rim 60 and adjacent to a portion of the barrier layer 40 not covered by the inward rim 60. According to one embodiment, the first portion 33 and second portion 34 can be formed in a two-shot molding process. The barrier layer 40 can be heat sealed, welded, and/or mechanically secured within the body 35 of the stopper 30. Additionally, the inward rim 60 can include apertures 70 extending therethrough and the top surface 42 of the barrier layer 40. The barrier layer 40 can be coined to the bottom surface 66 of the inward rim 60 or to the stopper material 33 by the application of sufficiently high stress to the assembly to induce plastic flow on the surface of the inward rim 60 and/or stopper material 33. The coining process will enable the barrier layer 40 to be positioned within the interior portion or body 35 of the stopper 30. The barrier layer 40 can be a plastic material such as HDPE, LDPP, or PET. According to one embodiment, the barrier layer 40 can be formed from the same material as the cap body 20. The barrier layer 40 can be applied within the stopper 30 by injecting the plastic barrier layer 40 with the first shot of stopper material and coined to this first shot of stopper material, over-molded onto a portion of the stopper 30, coined at the same time as the molding step, or applied to the second shot of stopper material in a two-shot molding process. According to yet another embodiment, each of the first and second portions 33, 34 of the stopper 30 can be molded and the barrier layer 40 can be separately assembled between the stopper components and coined to one or both of the first and second portions 33, 34. According to one embodiment, the barrier layer 40 can have an initial thickness of approximately 0.02 mm which is then pressed or coined to a thickness of approximately 0.003 mm. It can be appreciated that the bather layer 40 must be thick enough to provide barrier properties to the stopper 30, but thin enough so that it can be pierced by the needle.

Referring back to FIGS. 1-2, the first material for forming the cap body 12 can be a hard material and the cap body 12 can include an outer surface configured for interfacing with an outside source, such as one's hand or a machine, to remove the closure from the container. This outer surface can include surface irregularities 13 to assist in gripping the closure. According to one embodiment, the first material forming the cap body 12, can be high density polyethylene (HDPE) or low density polyethylene (LDPE), the second material forming the stopper 30 can be a thermoplastic elastomer, such as a thermoplastic elastomer capable of resealing after piercing by a needle cannula, and the third material forming the barrier layer 40 can be a film or a foil layer. The barrier layer 40 may be a polymeric and/or metal based film or foil structure. The barrier layer 40 can have a thickness of approximately 0.005 mm and can be formed from polyethylene terephthalate (PET) or ethylene vinyl alcohol (EVOH). According to one embodiment, the third material can comprise a multi-layer laminate having a central layer formed from polyethylene terephthalate (PET) or ethylene vinyl alcohol (EVOH) sandwiched between a pair of polyethylene layers. It can be appreciated that the first, second, and third materials can be formed from other well-known materials having the appropriate physical characteristics to perform their intended function.

The specimen sample container 10 can be an evacuated container and the third material forming the barrier layer 40 can be formed of a material that enhances the oxygen barrier properties of the evacuated container 10. The barrier layer 40 may substantially reduce the transition of oxygen therethrough, and may be thus substantially oxygen-impermeable. The use of barrier layer 40 can result in the reduction in the amount of thermoplastic elastomer material or second material used to form the stopper 30, resulting in a reduction in materials cost. The barrier layer 40 can include one or more of a weak spot, a cross-cut, and a slit 48 (FIGS. 3-7) to facilitate entrance of a needle cannula therethrough during collection of a specimen sample.

In accordance with another embodiment of the present invention, a method for forming a closure 12 for closing and sealing a container 10 includes providing a cap body 20 formed from a first material, the cap body 20 defining a cavity 24 therethrough and having a top portion or a second leg 20b defining an opening 28, the cavity 24 being in communication with the opening 28. The method further includes providing a stopper 30 formed from a second material and disposed within the cavity 24. The stopper 30 is configured for sealing the container 10 and for resealing after puncturing by a needle. The method also includes providing a barrier layer 40 formed from a third material and associated with at least one of the cap body 20 and the stopper 30. The bather layer 40 is configured for cooperating with the stopper 30 to seal the container 10. The method further includes assembling the cap body 20, the stopper 30, and the barrier layer 40 together to form a one-piece closure 12.

In accordance with another embodiment of the present invention, reference is made to FIGS. 1-2 which show a container assembly, generally indicated as 100, that includes a collection container 10 having a closed bottom 14, an open top portion 16, and a sidewall 18 extending therebetween. The container 10 is adapted to receive a specimen sample therein. The container assembly 100 includes a closure assembly 12 for closing and sealing the open top portion 16 of the collection container 10. The closure assembly 12 comprises a cap body 20 formed from a first material, the cap body defining a cavity 24 therethrough. The cap body 20 includes a first leg 20a configured for cooperating with the sidewall 18 of the container 10 to secure the cap body 20 thereto. The cap body 20 also has a top portion or a second leg 20b defining an opening 28 wherein the cavity 24 is in communication with the opening 28. The closure assembly 12 further includes a stopper 30 formed from a second material and disposed within the cavity 24. The stopper 30 is configured for sealing the container 10 and for resealing after puncturing by a needle. The closure assembly 12 further includes a barrier layer 40 formed from a third material and associated with at least one of the cap body 20 and the stopper 30 wherein the barrier layer 40 is configured for cooperating with the stopper to seal the container 10.

It can be appreciated that each of the embodiments disclosed above result in a closure assembly having increased oxygen barrier properties to assist in the containment of a predetermined vacuum draw within an evacuated container. It can also be appreciated that each of the embodiments disclosed above can be formed as a one-piece assembly reducing manufacturing and assembly costs. While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention.

The invention claimed is:

1. A closure, comprising:
    a cap body formed from a first material, the cap body defining a cavity therethrough and including an inward rim extending into the cavity;
    a stopper formed from a second material and disposed within the cavity, at least a portion of the stopper contacting at least a portion of the inward rim, the second material being different than the first material, wherein the second material has resealing capabilities; and
    a barrier layer formed from a third material, the third material being different from at least the second material, wherein the barrier layer divides the stopper into a first portion and a second portion such that the barrier layer contacts and is secured to the inward rim and the stopper and wherein a portion of the barrier layer is sandwiched between at least one of the first portion and the second portion of the stopper and the inward rim of the cap body to mechanically lock the barrier layer therebetween.

2. The closure of claim 1, wherein the third material is different from the second material and the first material.

3. The closure of claim 1, wherein the barrier layer is disposed across at least a portion of the cavity.

4. The closure of claim 1, wherein the barrier layer isolates a portion of the cap body from a portion of the stopper.

5. The closure of claim 1, wherein the cap body, the stopper, and the barrier layer are formed in a multi-shot molding process.

6. The closure of claim 1, wherein the barrier layer is heat sealed to at least one of the inward rim and the stopper.

7. The closure of claim 1, further comprising a seal ring positioned within an opening defined by a top portion of the cap body and adjacent the barrier layer.

8. The closure of claim 7, wherein the inward rim is a stepped member having a first portion for receiving a portion of the stopper and a second portion for contacting the barrier layer, wherein the barrier layer is sandwiched between the seal ring and the second portion.

9. The closure of claim 1, wherein the barrier layer includes a bottom surface positioned adjacent a top portion of the inward rim and the first portion of the stopper is positioned adjacent a top surface of the barrier layer to mechanically lock the barrier layer within a portion of the closure.

10. The closure of claim 1, wherein a portion of the inward rim includes apertures extending therethrough and a top surface of the barrier layer is secured to a bottom surface of the inward rim.

11. The closure of claim 1, wherein the cap body and the stopper are formed in a two-shot molding process and the barrier layer is applied in a post-molding process.

12. The closure of claim 11, wherein the barrier layer is applied to cover at least a portion of an opening defined by a top portion of the cap body and/or a top portion of the first or second portions of the stopper.

13. The closure of claim 1, wherein the stopper is formed in a two-shot molding process and the barrier layer is applied within a body of the stopper.

14. The closure of claim 13, wherein the barrier layer is secured to one of the first portion and the second portion such that, when assembled, the barrier layer is located within the body of the stopper.

15. The closure of claim 14, wherein the barrier layer is supplied during a first shot of the two-shot molding process.

16. The closure of claim 14, wherein the barrier layer is supplied during a second shot of the two-shot molding process.

17. The closure of claim 14, wherein the barrier layer is secured to at least one of the first portion and the second portion of the stopper in an overmolding process.

18. The closure of claim 14, wherein a top portion of the stopper, the barrier layer, and a bottom portion of the stopper are separately assembled and wherein the barrier layer is secured to at least one of the first portion and the second portion of the stopper.

19. The closure of claim 1, wherein the stopper is formed in a molding process and the barrier layer is secured to the stopper simultaneously with the molding process.

20. The closure of claim 1, wherein the barrier layer is substantially oxygen impermeable.

21. The closure of claim 1, wherein the first material comprises at least one of high density polyethylene (HDPE) and low density polyethylene (LDPE).

22. The closure of claim 1, wherein the second material comprises a thermoplastic elastomer.

23. The closure of claim 22, wherein the thermoplastic elastomer is free from di(2-ethylhexyl)phthalate (DEHP).

24. The closure of claim 23, wherein the third material comprises a multi-layer laminate having a central layer formed from polyethylene terephthalate (PET) or ethylene vinyl alcohol (EVOH) sandwiched between at least two polyethylene layers.

25. The closure of claim 1, wherein the third material is at least one of a polymeric and metal based film or foil structure.

26. The closure of claim 25, wherein the third material has a thickness of approximately 0.005 mm.

27. The closure of claim 1, wherein the third material comprises polyethylene terephthalate (PET) or ethylene vinyl alcohol (EVOH).

28. The closure of claim 1, wherein the barrier layer includes at least one of a weak area, a cross-cut, or a slit.

29. A container assembly, comprising:
   a collection container having a closed bottom, an open top portion, and a sidewall extending therebetween, the collection container defining an interior adapted to receive a specimen sample therein; and
   a closure for closing the open top portion of the collection container, comprising:
      a cap body formed from a first material, the cap body defining a cavity therethrough and including an inward rim extending into the cavity;
      a stopper formed from a second material and disposed within the cavity, at least a portion of the stopper contacting at least a portion of the inward rim, the second material being different from the first material, wherein the second material has resealing capabilities; and
      a barrier layer formed from a third material, the third material being different from at least the second material, wherein the barrier layer divides the stopper into a first portion and a second portion such that the barrier layer contacts and is secured to the inward rim and the stopper and wherein a portion of the barrier layer is sandwiched between at least one of the first portion and the second portion of the stopper and the inward rim of the cap body to mechanically lock the barrier layer therebetween.

30. The container assembly of claim 29, wherein the barrier layer is disposed across at least a portion of the cavity.

31. The container assembly of claim 29, wherein the barrier layer isolates a portion of the cap body from a portion of the stopper.

32. The container assembly of claim 29, wherein the barrier layer is substantially oxygen impermeable.

33. A method of forming a closure for closing and sealing a container, said method comprising:
   providing a cap body formed from a first material, the cap body defining a cavity therethrough and including an inward rim extending into the cavity;
   providing a stopper formed from a second material and disposed within the cavity, at least a portion of the stopper contacting at least a portion of the inward rim, the second material being different than the first material, wherein the second material has resealing capabilities;

providing a barrier layer formed from a third material, the third material being different from at least the second material; and assembling the cap body, the stopper, and the barrier layer together to form the closure such that the barrier layer divides the stopper into a first portion and a second portion such that the barrier layer contacts and is secured to the inward rim and the stopper and wherein a portion of the barrier layer is sandwiched between at least one of the first portion and the second portion of the stopper and the inward rim of the cap body to mechanically lock the barrier layer therebetween.

34. The method of claim 33, wherein the cap body, the stopper, and the barrier layer are formed in a multi-shot molding process.

35. The method of claim 33, wherein the cap body and the stopper are formed in a two-shot molding process and the barrier layer is applied in a post-molding process.

36. The method of claim 33, wherein the barrier layer is applied to cover at least a portion of an opening defined by a top portion of the cap body and/or a top portion of the stopper.

37. The method of claim 33, wherein the barrier layer is at least one of heat sealed, secured with a seal ring, and mechanically sealed to at least one of the cap body and stopper.

38. The method of claim 33, wherein the barrier layer is provided on a bottom surface of the stopper.

39. The method of claim 33, wherein the barrier layer is substantially oxygen impermeable.

40. The closure of claim 1, wherein a portion of the barrier layer is exposed.

* * * * *